United States Patent [19]

Cvetovich

[11] Patent Number: 5,288,710
[45] Date of Patent: Feb. 22, 1994

[54] STABLE SALTS OF 4″-DEOXY-4″-EPI-METHYLAMINO AVERMECTIN BLA/BLB

[75] Inventor: Raymond Cvetovich, Scotch Plains, N.J.

[73] Assignee: Merck & Co., Inc., Rahway, N.J.

[21] Appl. No.: 862,035

[22] Filed: Apr. 2, 1992

Related U.S. Application Data

[63] Continuation of Ser. No. 545,229, Jun. 28, 1990, abandoned.

[51] Int. Cl.$^5$ .................. A61K 31/70; C07H 17/04
[52] U.S. Cl. .......................... 514/30; 536/7.1
[58] Field of Search ................... 536/7.1; 514/30

[56] References Cited

U.S. PATENT DOCUMENTS

| | | | |
|---|---|---|---|
| 4,321,361 | 3/1982 | Baltz et al. | 536/7.1 |
| 4,366,309 | 12/1982 | Ganguly et al. | 536/7.1 |
| 4,427,663 | 6/1984 | Mrozik | 514/30 |
| 4,831,016 | 5/1989 | Mrozik et al. | 514/30 |
| 4,874,749 | 10/1989 | Mrozik | 514/30 |

FOREIGN PATENT DOCUMENTS 301806 2/1989 European Pat. Off. .

OTHER PUBLICATIONS

Experentia, 45, pp. 315-316 (1989) Mrozik, et al.

Primary Examiner—Johnnie R. Brown
Assistant Examiner—Elli Peselel
Attorney, Agent, or Firm—David L. Rose; Joseph F. DiPrima; Valerie J. Camara

[57] ABSTRACT

Certain salts of 4″-deoxy-4″-epi-methylamino avermectin Bla/Blb such as: the benzoic acid salt, gallic acid salt, citric acid salt, benzenesulfonic acid salt and salicyclic acid salt, phosphoric acid salt, tartaric acid salt or maleic acid salt, exhibit enhanced stability, a property which serves to provide greater shelf life and a product of greater safety for the user and the environment.

4 Claims, No Drawings

STABLE SALTS OF 4"-DEOXY-4"-EPI-METHYLAMINO AVERMECTIN BLA/BLB

This is a continuation of application Ser. No. 07/545,229, filed Jun. 28, 1990, now abandoned.

BACKGROUND OF THE INVENTION

U.S. Pat. No. 4,427,663 to Mrozik describes the synthetic routes used to prepare 4"-deoxy-4"-amino avermectin Bla/Blb and substituted amino avermectins. U.S. Pat. No. 4,874,749 published Oct. 17, 1989, discloses the 4"-deoxy-4"-epi-methylamino avermectin hydrochloride as having properties as an agricultural insecticide. The enhanced stability of the compounds of the present invention over the known hydrochloride salt will give this agricultural insecticide a longer shelf life.

DETAILED DESCRIPTION OF THE INVENTION

This invention is concerned with an acid addition salt of a mixture of compounds named as 4"-deoxy-4"-epi-methylamino avermectin Bla/Blb which is best described by the following structural formula:

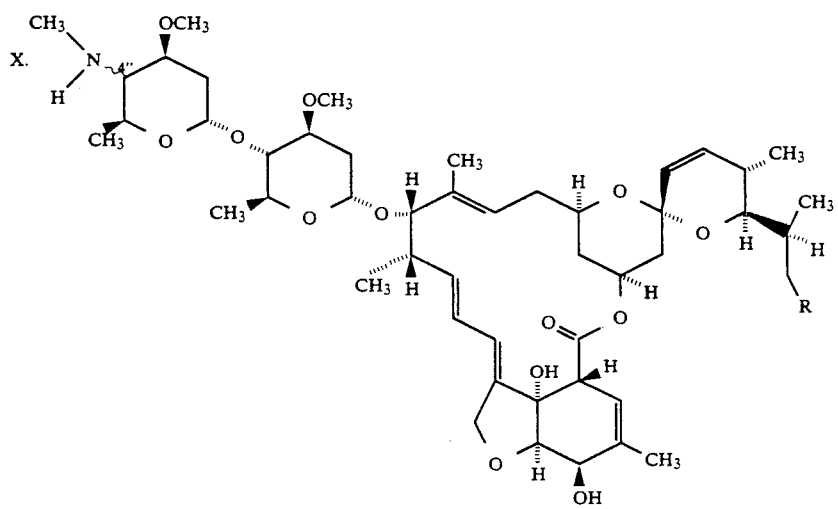

wherein:
R is hydrogen or methyl; and
X is:
  a) benzoic acid,
  b) benzoic acid substituted with one, two, or three substituents selected from the group consisting of:
    i) halogen (Cl, Br, F, I),
    ii) hydroxyl,
    iii) carboxyl,
    iv) ($C_1$-$C_6$)-alkyl, and
    v) ($C_1$-$C_6$)-alkoxyl,
  c) benzenesulfonic acid,
  d) citric acid,
  e) phosphoric acid,
  f) tartaric acid, or
  g) maleic acid.

When R is a methyl group, the compound is 4"-deoxy-4"-epi-methylamino avermectin Bla and where R is hydrogen, the compound is 4"-deoxy-4"-epi-methylamino avermectin Blb.

The preferred acid addition salts are formed with benzoic acid, salicyclic acid, gallic acid, benzenesulfonic acid and citric acid.

The most preferred acid addition salt is that formed with benzoic acid.

The stability studies indicate the benzoic acid salt is more stable than the corresponding hydrochloride salt. The benzoic acid salt as shown in Table 2 of Example 12 shows virtually no change after 32 weeks at room temperature and at 47° C. in the first and a slight drop at 47° C. in the second sample. The data for the benzoic acid salt (Table 2 of Example 12) when compared with the hydrochloride salt (Table 1 of Example 12) indicates the benzoic acid salt is markedly more resistant to degradation. The data also indicates, in Table 3 of Example 13, the benzoic acid salt after 32 weeks at room temperature and 47° C. is more resistant to degradation than the phosphate, tartrate, citrate, gallate, salicylate, benzenesulfonate or maleate salts, which at 8 weeks have suffered less degradation than the hydrochloride. The benzenesulfonate and maleate salts indicate a drop in percent purity at 47° C. after 16 weeks, however the benzoate salt shows no change after 32 weeks at 47° C.

Generally the compounds of the instant invention are used as a mixture of the two compounds, Bla and Blb, since the structural differences are very slight and amount to the difference between a sec-butyl group and an isopropyl group, and the two compounds have substantially the same chemical reactivity and biological activities.

For convenience, the nomenclature Bla/Blb is employed to indicate the individual compounds and the mixture of such compounds.

The above compounds exist in two stereochemical forms where the methylamino group is below the plane of the ring ($\alpha$) or above the plane of the ring ($\beta$), the epi-isomer. During the preparation of the compound the $\beta$-compound is prepared in greater abundance than the $\alpha$-compound. In testing both compounds however, they are observed to have substantially the same biological activity.

The instant compound is prepared from avermectin Bla/Blb, which has the 4"-hydroxy in place of the 4"-epi-methylamino substituent. Isolation of avermectin Bla/Blb from fermentation broth is described in U.S. Pat. No. 4,310,519 issued on Jan. 12, 1982. Further elaboration of the above compound can be accomplished utilizing a synthetic route set forth in U.S. Pat. No. 4,427,663 for the preparation of 5-O-t-butyldimethylsilyl-4"-oxo-22,23-dihydro avermectin. The 4"-keto undergoes reductive amination with sodium cyanoborohydride and the appropriate amine. The same synthetic route has been employed to prepare 4"-deoxy-4"-epi-methylamino avermectin Bla/Blb.

The 4"-deoxy-4"-epi-methylamino avermectin Bla/Blb is derived from avermectin Bla/Blb which is a compound with a hydroxy group at the 4" position. This compound is oxidized to the ketone which in turn is reductively aminated with methylamine to form the 4"-deoxy-4"-methylamino group. During the process the α-configuration of the original hydroxy group is significantly inverted to the β-position which thus results in the 4"-deoxy-4"-methylamino substituent being obtained in less quantity than the major product 4"-deoxy-4"-epi-methylamino avermectin Bla/Blb. The reaction is illustrated in the following reaction scheme wherein only the terminal α-L-oleandrosyl molecule group is shown. The remainder of the molecule is unchanged and is as shown in Structure I.

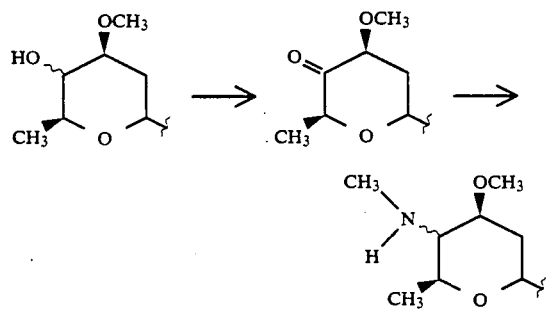

In the first step of the above reaction scheme, avermectin Bla/Blb is oxidized to the 4"-oxo compound. During the procedure the 5-hydroxy group should be protected to prevent multiple reactions. The preferred protecting group is the t-butyl-dimethylsilyl group. In the oxidation of the 5-O-protected avermectin Bla/Blb oxalyl chloride or trifluoroacetic anhydride in dimethylsulfoxide, N-chlorosuccinimide in dimethyl sulfide, and the like may be employed. The reaction is generally carried out in an inert solvent such as methylene chloride from −50° to −80° C. and is generally complete in less then 2 hours. The product is isolated using known techniques. In the next step the 4"-keto compound is aminated with methylamine salts, preferably methyl amine acetate, to form the 4"-methylamino substituent. The reaction is carried out at about −25° to +10° C. in an inert solvent such as a lower alkanol. The methyl ammonium salt complex is reduced using, for example, sodium cyanoborohydride to form the 4"-deoxy-4"-methylamino compound. The compound is isolated using techniques known to those skilled in the art.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridis, Oxyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs; Namatospiroides, Syphacia, Aspiculuris in rodents; the arthropod ectoparasites of animals and birds such as ticks, mites, lice, fleas, and blowfly; in sheep Lucilia sp.; biting insects and such migrating diperous larvae as Hypoderma sp. in cattle; Gastrophilus in horses; and Caterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and, other dipterous pests causing annoyance to man.

The compounds are also active against household pests such as the cockroach, Blatella sp., clothes moth, Tineola sp., Carpet beetle, Attagenus sp., and the housefly Musca domestica.

The compounds are also useful against insect pests of stored grains such as Tribolium sp., Tenebrio sp., and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with suspending agent such as bentonite and a wetting agent or like excipient. Generally, the drenches also contain an antifoaming agent, Drench formulations generally contain from about 0.001 to 0.5% by weight of the active compound. Preferred drench formulations may contain from 0.01 to 0.1% by weight.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of the invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice fleas, mites and other biting insects in domesticated animals and poultry. They are also effective in treatment of parasitic diseases that occur in other animals including humans.

The optimum amount to be employed for best results will, of course, depend upon the particular compound employed, the species of animal to be treated and the type and severity of parasitic infection or infestation. Generally good results are obtained with the novel compounds by the oral administration of from about 0.001 to 10 mg per kg of animal body weight, such total dose being given at one time or in divided doses over a relatively short period of time such as 105 days. With the preferred compounds of the invention, excellent control of such parasties is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The 4"-epi-methylamino salt compounds of the present invention are valuable antibiotics active against various Gram-positive and Gram-negative bacteria and accordingly find utility in human and veterinary medicine. Representative pathogens which are sensitive to the instant compounds include: *Staphylococcus aureus, Escherichia coli, Klebsiella pneumonise, Bacilhus subtilis, Salmonella typhosa,* Psuedomones and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may also be used in any of a variety of pharmaceutical preparations. They may be employed in capsule, powder form, in liquid solution, or in suspension. They may be administered by a variety of means; those of principle interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerine.

Composition for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 0.1 to about 5 mg of active ingredient per kg. of body weight of the subject in one or more treatments per day. A preferred daily dosage for adult humans lies in the range of from about 0.1 to 20 mg of active ingredient per kg. of body weight. Another factor influencing the precise dosage regimen, apart from the nature of the infection and peculiar identity of the individual being treated, is the molecular weight of the carbon species of this invention.

The compositions for human delivery per unit dosage, whether liquid or solid, may contain from 0.1% to 99% of active material, the preferred range being from about 10-60% The composition will generally contain from about 5 mg to about 50 mg of the active ingredient; however, in general, it is preferable to employ a dosage amount in the range of from about 5 mg to 100 mg. In parenteral administration, the unit dosage is usually the pure compound I in sterile water solution or in the form of a soluble powder intended for solution.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin Bla or Ala and 20% avermectin Blb or Alb. Thus the preferred composition of this invention is one which contains about 80% of the "a" component and 20% of the "b" component.

The following examples are provided in order that the invention might be more fully understood. The examples are not to be construed as limitations upon the scope of the invention.

EXAMPLE 1

5-O-t-Butyldimethylsilyl avermectin Bla/Blb

A solution of 50 g of avermectin Bla/Blb (dried over $P_2O_5$ in high vacuum to constant weight), 24 g of imidazole and 24 g of tert-butyldimethylsilyl chloride in 400 ml of anhydrous N,N-dimethylformamide was stirred at room temperature for 50 minutes. The reaction mixture was poured into 1.5 l of ice cold water and the aqueous phase was extracted four times with 200 ml of ether. The organic phase was washed twice with water, aqueous sodium chloride solution, dried with magnesium sulfate and concentrated in vacuo to a white foam. The crude product was purified by silica gel column chromatography with a methylene chloride:ethyl acetate, 90:10 to 70:30 solvent system to give 46.5 g of 5-O-t-butyldimethylsilyl avermectin Bla/Blb as an amorphous foam, which was characterized by its $^1$H-NMR and mass spectra.

EXAMPLE 2

5O-t-Butyldimethylsilyl-4"-oxo avermectin Bla/Blb

To a solution containing 9.1 ml of oxalyl chloride in 230 ml of dry methylene chloride stirred at −60° C. was added 15 ml of dry dimethylsulfoxide dissolved in 120 ml of dry methylene chloride during 15 min. Then a solution of 46.5 g of 4-O-t-butyldimethylsilyl avermectin Bla/Blb dissolved in 230 ml of dry methylene chloride was added over a period of 15 minutes while maintaining the temperature at −60° C. The reaction mixture was stirred at this temperature for 30 minutes when 65 ml of dry triethylamine was added. The mixture was stirred for 5 additional minutes at −60° C., the cooling bath was removed and the reaction mixture was allowed to come to ambient temperature. After addition of water the reaction product was extracted with methylene chloride, the extract was washed with water, dried and concentrated in vacuo to 45.5 g of a yellow foam. This was identified by its mass and NMR spectra as 5-O-t-butyldimethylsilyl-4''-oxo avermectin B1a/B1b, which was used for further chemical reactions without purification.

EXAMPLE 3

4''-Deoxy-4''-epi-methylamino-5-O-t-butyldimethylsilyl avermectin B1a/B1b and 4''-deoxy-4''-methylamino-5-O-t-butyldimethylsilyl avermectin B1a/B1b A solution of 26 ml of glacial acetic acid in 300 ml of methanol was treated with methylamine gas at 0° C. until the pH of the solution reached 9.0. To this a solution containing 44.5 g of 5-O-t-butyldimethylsilyl-4''-oxo avermectin B1a/B1b in 200 ml of methanol was added, and the reaction mixture was stirred at room temperature for 1 hour, when a solution of 3.5 g of sodium cyanoborohydride in 75 ml of methanol was added dropwise over 10 minutes. After 50 minutes the reaction mixture was poured into 1.5 l of cold aqueous sodium carbonate solution and the product was extracted with ether. The extract was washed with water, dried, and concentrated in vacuo to 44.8 g of yellow foam. Thin layer chromatography (silica gel, ethyl acetate: methylene chloride, 85:15) of the crude product at this point shows several spots. Further purification by silica gel column chromatography using ethyl acetate solvent mixtures gave 4.7 g of 5-O-t-butyldimethylsilyl-4''-epi-avermectin B1a/B1b, 1.2 g of 4''-deoxy-4''-methylamino-5-O-t-butyldimethylsilyl avermectin B1a/B1b, and 14 g of 4''-deoxy-4''-epi-methylamino-5-O-t-butyldimethylsilyl avermectin B1a/B1b as light foams, which were characterized by their mass spectrum and their $^1$H-NMR, and $^{13}$C-NMR spectra.

EXAMPLE 4

4''-Deoxy-4''-epi-methylamino avermectin B1a/B1b

A solution of 14 g of 4''-deoxy-4''-epi-methylamino-5-O-t-butyldimethylsilyl avermectin B1a/B1b in 200 ml of methanol and a solution of 7 g of p-toluenesulfonic acid monohydrate in 500 ml of methanol was mixed and stirred at room temperature for 45 minutes, and then poured into dilute aqueous sodium carbonate solution. The product was extracted with ethyl acetate, washed with water and dried over magnesium sulfate, concentrated in vacuo, and purified by preparative silica gel column chromatography with a methylene chloride/methanol 95:5 solvent mixture to give 6.7 g of 4''-deoxy-4''-epi-methylamino avermectin B1a/B1b, which was identified by NMR and mass spectra.

EXAMPLE 5

4''-Deoxy-4''-epi-methylamino avermectin B1b/B1a Phosphoric Acid Salt

4''-Deoxy-4''-epi-methylamino avermectin (2.34 g, 2.64 mm) was dissolved into acetonitrile (10 ml). A solution of phosphoric acid (0.292 g, 3.00 mm) in acetonitrile (5 ml) was added and the mixture formed a dense precipitate. The suspension was diluted with 10 ml acetonitrile and stirred vigorously for one hour. The suspension was filtered, washed with acetonitrile (10 ml) and dried in vacuo overnight at 45° C. The salt, a white solid was isolated in 2.36 gm, and proved to be amorphous. The salt (2.25 gm) was suspended in acetonitrile (10 ml), methanol was added to completely dissolve the salt, and then diluted with 25 ml toluene. The resultant solution was cooled to 0°-2° C. and crystallization ensued. After a 2-hour age the crystals were filtered, washed with acetonitrile/toluene (1:2), cooled to 5° C. and dried in vacuo to give 1.81 g of 4''-deoxy-4''-epi-methylamino avermectin B1a/B1b phosphoric acid salt.

Molecular Weight: 984
Melting Point: 158° C. (yellowing)—163° C. (dec)
Titration (base): 2.16 meq/gm=1:1 salt
Microanalysis: calculated: C, 59.81; H, 7.99; N, 1.42; P, 3.15. found: C, 58.80; H, 8.25; N, 1.39; P, 3.03.
X-Ray indicated material was non-crystalline.

EXAMPLE 6

4''-Deoxy-4''-epi-methylamino avermectin B1b/B1a Benzenesulfonic Acid Salt

4''-Deoxy-4''-epi-methylamino avermectin (2.34 g, 2.64 mm) was dissolved into acetonitrile (10 ml). A solution of benzenesulfonic acid (0.413 g, 2.61 mm) in acetonitrile (5 ml) was added and the mixture was diluted with toluene (15 ml). The resultant solution was cooled to 0°-2° C. and crystallization ensued. After a 2-hour age the crystals were filtered, washed with acetonitrile/toluene (1:1) cooled to 5° C. and dried in vacuo to give 1.81 g of 4''-deoxy-4''-epi-methylamino avermectin B1a/B1b benzenesulfonic acid salt.

Molecular Weight: 1044
Melting Point: 154°-156° C. (decomposed)
Microanalysis: calculated: C, 63.28; H, 7.82; N, 1.34; S 3.07. found: C, 63.45; H, 8.05; N, 1.36; S, 3.28.

EXAMPLE 7

4''-Deoxy-4''-epi-methylamino avermectin B1b/B1a Maleic Acid Salt

4''-Deoxy-4''-epi-methylamino avermectin B1a/B1b (2.65 g, 3.06 mm) in acetonitrile (10 ml) was treated with maleic acid (0.356 g, 3.00 mm), and then diluted with toluene (30 ml). Upon cooling to 0°-2° C. crystallization ensued. After aging for 2 hours, the crystals were filtered, washed with acetonitrile/toluene (1:2) and dried in vacuo at 55° C. to give 1.53 g at 4''-deoxy-4''-epi-methylamino avermectin B1a/B1b maleic acid salt (1:1 salt)

Molecular Weight: 1002
Melting Point: 155°-160° C. (decomposed)
Titration (base): 2.01 meq/gm=1:1 salt
Microanalysis: calculated: C, 63.57; H, 7.95; N, 1.40. found: C, 63.04; H, 8.15; N, 1.40.

EXAMPLE 8

4''-Deoxy-4''-epi-methylamino avermectin B1b/B1a Citric Acid Salt

4''-Deoxy-4''-epi-methylamino avermectin B1a/B1b (2.65 g, 3.06 mm) was dissolved in acetonitrile (10 ml) and methanol (1 ml), to which was added citric acid (0.572 g, 2.98 mm). Toluene (20 ml) was added and the solution was cooled to 0°-2° C. Upon crystallization, the mixture was aged 2.0 hours, filtered, washed with acetonitrile/toluene (1:2) and dried in vacuo at 45° C. to give 3.03 gm of 4''-deoxy-4''-epi-methylamino avermectin B1a/B1b citric acid salt (1:1).

Molecular Weight: 1078
Melting Point: 148° C. yellowing—162° C. (dec)
Titration (base): 2.70 meq/gm=1:1 salt.

Microanalysis: calculated: C, 61.28; H, 7.76; N, 1.30. found: C, 61,30; H, 8.04; N, .1.27.

EXAMPLE 9

4"-Deoxy-4"-epi-methylamino avermectin Blb/Bla Gallic Acid Salt

4"-Deoxy-4"-epi-methylamino avermectin Bl (2.66 g, 3.07 mm) was dissolved into acetonitrile (10 ml). Added gallic acid (0.51 g, 3.00 mm) dissolved into methanol (0.5 ml). Aged at 25° C. to give crystals. Added toluene (10 ml) and aged 30 min. The crystals were filtered, washed with 10 ml acetonitrile/toluene (1:1) and dried in vacuo to give 2.64 gm of 4"-deoxy-4"-epi-methylamino avermectin Blb/Bla gallic acid salt.

Molecular Weight: 1056
Melting Point: 160° C. (yellowing)—186° C. (dec)
Microanalysis: calculated: C, 63.70; H, 7.73; N, 1.33. found: C, 63.21; H, 7.92; N, 1.61.

EXAMPLE 10

4"-Deoxy-4"-epi-methylamino avermectin Blb/Bla Benzoic Acid Salt

4"-Deoxy-4"-epi-methylamino avermectin Bla/Blb (5.10 kg, 5.75 m) in tert-butylmethyl ether (18 L) was treated with benzoic acid (755 g, 6.18 m) at 25° C. To this solution was added hexanes (36 L) over a 0.5–1.0 hour period, whereupon crystallization occurs during the addition. The crystalline slurry was cooled to 0°–2° C., aged for 1 hour at 0°–2° C. then filtered. The filter cake was then washed with a mixture of tert-butylmethyl ether/hexanes (1:2) and dried in vacuo at 60° C. to give 5.7 kg of 4"-deoxy-4"-epi-methylamino avermectin Bla/Blb benzoic acid salt.

Molecular Weight: 1008
Melting Point: 133°–136° C.
Microanalysis: calculated: C, 66.71; H, 8.10; N, 1.39 found: C, 66.93; H, 8.32; N, 1.20

EXAMPLE 11

4"-Deoxy-4"-epi-methylamino avermectin Blb/Bla Salicyclic Acid Salt

4"-Deoxy-4"-epi-methylamino avermectin $B_1$ (2.65 g, 3.04 mmol) was dissolved into acetonitrile (10 ml). Salicylic acid (0.415 g, 3.00 mmol) was added to give a homogeneous solution. Toluene (30 ml) was added and the solution was reduced to ⅓ volume by distillation in vacuo whereupon crystal formation ensued. The slurry was evaporated in vacuo and the solids reslurried with acetonitrile/toluene (3 ml: 10 ml). The crystals were filtered, washed with acetonitrile/toluene (5 ml, 10 ml resp.) and dried in vacuo to give 3.01 g of 4"-deoxy-4"-epi-methylamino avermectin Blb/Bla salicyclic acid salt.

Melting Point: 161°–163° C. (yellowing)
Molecular Weight: 1024
Microanalysis: calculated: C, 65.69; H, 7.97; N, 1.37. found: C, 67.49; H, 8.28; N, 1.27.

EXAMPLE 12

Stability studies on the benzoic acid salt versus the hydrochloride salt of 4"-Deoxy-4"-epi-methylamino avermectin Bla/Blb A sample of the product of Example 10, the benzoic acid salt, was tested against the hydrochloride salt to determine the relative stability of the avermectin salt. Samples of the HCl salt and benzoic acid salt were kept at −10° C., room temperature and 47° C. A sample of the salts was kept at −10° C. and used as a control. The degradation of the salts in air, at room temperature and 47° C. over time are measured by HPLC against the freezer sample. The area % of the degradation products versus the starting material was determined using the following HPLC conditions:

Column: Vydac 5 μm C18 protein with 300 angstrom pore diameter (catalog 218 Tp) 15 cm long X 4.6 mm ID
Temperature: Ambient
Detection: UV at 245 nm and 0.1 AUFS
Flow Rate: 3 ml/min
Inj. Volume: 10 μl
Eluants: 1) A=0.1% perchloric acid in water (v/v); B=acetonitrile or 2) A=0.1% trifluoroacetic acid in water; B=0.1% trifluoroacetic acid in acetonitrile (the trifluoroacetic acid solvent system made it harder to balance the UV)
Gradient: 65/35 A/B to 38/62 A/B in 30 minutes
Sample: 30 mg/100 ml in 90/10 acetonitrile/water Under the conditions the retention time of the Blb peak is 10.6 minutes and that of the Bla is 12.5 minutes. When better resolution of the earlier peaks was desired the gradient was slowed down from 65/35 A/B to 55/45 A/B in 50 minutes.

Tables 1 and 2 show the results of the stability study on the HCl salt (Table 1) and the benzoic acid salt (Table 2).

TABLE 1

Stability Data for the Hydrochloride Salt of 4"-Deoxy-4"-epi-methylamino avermectin

| | HPLC WT % B1 | |
|---|---|---|
| Time (weeks) | RT (Air) | 47° C. (Air) |
| 0 | 100 | 100 |
| 4 | 82.0 | 71.4 |
| 8 | 72.4 | 61.5 |

TABLE 2

Stability Data for the Benzoic Acid Salt of 4"-Deoxy-4"-epi-methylamino avermectin Bla/Blb

| | HPLC WT % B1 | |
|---|---|---|
| Time (Weeks) | RT (Air) | 47° C. (Air) |
| Sample 1 | | |
| 4 | 98.1 | 99.7 |
| 8 | 101.6 | 105.4 |
| 16 | 100.9 | 101.2 |
| 32 | 101.2 | 100.7 |
| Sample 2 | | |
| 4 | 100.7 | 99.9 |
| 8 | 100.1 | 98.5 |

EXAMPLE 13

Stability study of the salts of 4"-Deoxy-4"-epi-methylamino avermectin Blb/Bla

Samples of the salts were analyzed using the HPLC conditions set forth in Example 12. The data for these samples are shown in Table 3.

TABLE 3

The Stability Data for the Salts of 4"-Deoxy-4"-epi-methylamino avermectin Blb/Bla

| | TIME | HPLC WT % B1 | |
|---|---|---|---|
| SALT | weeks | RT (Air) | 47° C. (Air) |
| Phosphate | 8 | 101.2 | 88.3 |
| Tartrate | 8 | 87.9 | 85.4 |
| Citrate | 8 | 99.2 | 92.7 |

TABLE 3-continued

The Stability Data for the Salts of 4"-Deoxy-4"-epi-methylamino avermectin B1b/B1a

| SALT | TIME weeks | HPLC WT % B1 RT (Air) | 47° C. (Air) |
|---|---|---|---|
| Gallate | 8 | 99.9 | 93.9 |
| Salicylate | 8 | 98.6 | 88.8 |
| Benzenesulfonate | 16 | 100.4 | 96.5 |
| Maleate | 16 | 98.7 | 93.7 |
| Benzoate (1) | 32 | 100.8 | 100.5 |
| Benzoate (2) | 32 | 101.2 | 100.7 |
| Benzoate (3) | 32 | 99.9 | 99.7 |
| Benzoate (4) | 32 | 100.2 | 100.8 |

What is claimed is:

1. A stable salt of Formula I:

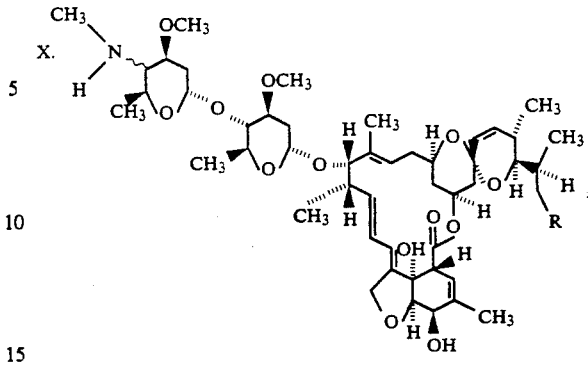

wherein:
R is hydrogen or methyl; and
X is: benzoic acid.

2. A method for the control of agricultural insects, which comprises applying to an area infested with such agricultural insects an effective amount of a stable salt of claim 1.

3. A composition useful for treating animals infected with parasites or insect infestations of plants or plant products which comprises an inert carrier and an effective amount of a stable salt of claim 1.

4. A method of treatment for parasitic infections in warm blooded animals, which comprises the administration of an effective amount of a stable salt of claim 1 to an animal in need of such treatment.

* * * * *